United States Patent [19]

Payne et al.

[11] Patent Number: 4,744,989
[45] Date of Patent: May 17, 1988

[54] METHOD OF PREPARING LIPOSOMES AND PRODUCTS PRODUCED THEREBY

[75] Inventors: Nicholas I. Payne; Peter Timmins, both of Merseyside; Cheryl V. Ambrose, London, all of United Kingdom

[73] Assignee: E. R. Squibb & Sons, Inc., Princeton, N.J.

[21] Appl. No.: 842,569

[22] Filed: Mar. 21, 1986

Related U.S. Application Data

[63] Continuation-in-part of Ser. No. 578,156, Feb. 8, 1984, abandoned, which is a continuation-in-part of Ser. No. 578,159, Feb. 8, 1984, abandoned.

[51] Int. Cl.$^4$ .............. A61K 9/16; A61K 37/22; A61K 9/50
[52] U.S. Cl. .......................... 424/490; 424/4; 424/5; 424/450; 424/491; 424/493; 514/3; 514/31
[58] Field of Search ............ 514/3, 31; 424/490, 424/491, 493, 450, 4, 5

[56] References Cited

U.S. PATENT DOCUMENTS

| 4,192,859 | 3/1980 | Mackaness et al. | 424/5 |
| 4,229,360 | 10/1980 | Schneider et al. | 260/403 |
| 4,247,411 | 1/1981 | Vanlerberghe et al. | 252/316 |
| 4,311,712 | 1/1982 | Evans et al. | 424/365 |
| 4,508,703 | 4/1985 | Redziniak et al. | 424/38 |

OTHER PUBLICATIONS

Ryman, B. E., "The Use of Liposomes as Carriers of Drugs and Other Cell-Modifying Molecules," Proc. 6th Int'l. Congr. Pharmacol. 5, 91 (1976).

Primary Examiner—Frederick E. Waddell
Attorney, Agent, or Firm—Lawrence S. Levinson; Burton Rodney

[57] ABSTRACT

A method is provided for preparing stable liposome precursors in the form of a water-soluble carrier material coated with a predetermined amount of a thin film of liposome components, which method includes the steps of dissolving at least one liposome-forming amphipathic lipid, optionally, at least one biologically active compound, and, optionally, at least one adjuvant in a suitable organic solvent and employing the resulting organic solution to coat a suitable water-soluble carrier material to form thin film of predetermined amount of liposome components thereon. Upon exposing the coated carrier material to water, the thin films of liposome components hydrate and the carrier material dissolves to give liposome preparations.

28 Claims, No Drawings

METHOD OF PREPARING LIPOSOMES AND PRODUCTS PRODUCED THEREBY

REFERENCE TO THE APPLICATION

This application is a continuation-in-part of U.S. patent applications Ser. Nos. 578,156 filed Feb. 8, 1984 and 578,159, filed Feb. 8, 1984.

FIELD OF THE INVENTION

The present invention relates to a method for preparing particulate water-soluble carrier materials coated with thin films of liposome components (also referred to as proliposomes), which coated carrier materials are employed to form liposome preparations, and to intermediates and products produced in such method.

BACKGROUND OF THE INVENTION

Liposomes are widely described in the literature and their structure is well known. They are formed by amphipathic molecules such as the class II polar lipids, that is, phosphatidyl cholines, ethanolamines and serines, sphingomyelins, cardiolipins, plasmalogens, phosphatidic acids and cerebrosides. Liposomes are formed when phospholipids or other suitable amphipathic molecules are allowed to swell in water or aqueous solutions to form liquid crystals usually of multilayer structure comprised of many bilayers separated from each other by aqueous material. Another type of liposome is known which is formed of a single bilayer encapsulating aqueous material which may also be referred to as a unilamellar vesicle. "If water-soluble materials are included in the aqueous phase during the swelling of the lipids they become entrapped between the lipid bilayers. Alternatively, lipid soluble materials may be dissolved in the lipid and, hence, may be incorporated into the lipid bilayers themselves," Ryman, B. E., "The Use of Liposomes as Carriers of Drugs and Other Cell-Modifying Molecules," Proc. 6th Int'l. Congr. Pharmacol. 5, 91 (1976), published in "Drug Applications," *Clinical Pharmacology,* Vol. 5, pp. 91–103, Pergamon Press (1975).

In recent years there has been much interest in the use of liposomes as carriers of compounds which are of interest because of one or other biological property, for example, medicaments, proteins, enzymes, hormones and diagnostic agents, hereinafter referred to as "biologically active compounds." Liposomes have been suggested as carriers for drugs, see Ryman, supra at page 91 and Gregoriadis, G., "Enzyme or Drug Entrapment in Liposomes: Possible Biomedical Application," *Insolubilized Enzymes,* Ed. M. Salmona et al, Raven Press, N.T. 1974, pp. 165–177.

Water-soluble materials are encapsulated in the aqueous spaces between the biomolecular layers. Lipid soluble materials are incorporated into the lipid layers although polar head groups may protrude from the layer into the aqueous space. The encapsulation of these compounds can be achieved by a number of methods. The method most commonly used involves casting a thin film of phospholipid onto the walls of a flask by evaporation of an organic solvent. When this film is dispersed in a suitable aqueous medium, multilamellar liposomes are formed (also referred to as coarse liposomes). Upon suitable sonication, the coarse liposomes form smaller similarly closed vesicles.

Water-soluble biologically active compounds are usually incorporated by dispersing the cast film with an aqueous solution of the compound. The unencapsulated compound is then removed by centrifugation, chromatography, dialysation or some other suitable procedure. Lipid-soluble biologically active compounds are usually incorporated by dissolving them in the organic solvent with the phospholipid prior to casting the film. Providing the solubility of these compounds in the lipid phase is not exceeded or the amount present is not in excess of that which can be bound to the lipid, liposomes prepared by the above method usually contain most of the compound bound in the lipid bilayers; separation of the liposomes from unencapsulated material is not required. Other methods of preparing liposomes have been described although these are mainly specialized methods producing unilamellar liposomes and include reverse-phase evaporation of an organic solvent from a water-in-oil emulsion of phospholipid, infusion of organic solutions of phospholipid into large volumes of aqueous phase and detergent removal from mixed micelles of detergent and lipid.

Aqueous liposome dispersions only have limited physical stability. The liposomes can aggregate and precipitate as sediment. Although this sediment may be redispersed, the size distribution may be different from that of the original dispersion. This may be overcome to some extent by incorporation of charged lipids into the liposomes. In addition, on storage the biologically active compounds may be lost into the external aqueous phase which restricts the potential of these preparations as practical dosage forms. This is particularly notable for low molecular weight water-soluble compounds but lipid soluble compounds too can partition into the external aqueous medium. If the volume of the aqueous medium is large, this loss can be significant. In addition, depending upon the type of lipid and biologically active compound present in the liposome, there is the potential for chemical degradation of the lipid components and/or the biologically active components in the aqueous dispersion.

These factors restrict the use of liposomes as practical carriers of biologically active compounds. One solution suggested for overcoming the limited physical stability of liposomes is to prepare and store the lipid/biologically active compound film and then disperse the film to form liposomes just prior to administration. However, unit dose film preparation presents serious practical difficulties in that the containers would require a high surface area to facilitate solvent evaporation and deposition of a thin film suitable for rapid dehydration to form liposomes readily. This type of container by virtue of its bulk would present severe storage problems. Other methods suggested for preparing liposome components in a solid form for storage have included freeze-drying the prepared aqueous liposome suspension as described in U.S. Pat. Nos. 4,229,360 to Schneider, et al. and 4,247,411 to Vanlerberghe and by freeze-drying the liposome components from a suitable organic solvent as described in U.S. Pat. No. 4,311,712 to Evans, et al. These freeze-dried preparations result in a porous matrix of liposome components which is easily hydrated.

It is known that the size of a liposome product could have a bearing on the delivery of a medicament, carried by the liposome product, to the desired site at the desired time. Thus, if the size of a liposome is too small, the liposome carrying the medicament may persist in the circulating plasma for an exceedingly long period and the medicament will not be delivered to the targeted site within the requisite time. If the size of the liposome is too large, the liposome can cause a capillary blockage and/or may be removed by untargeted tissue. Thus, where the medicament carried by the liposome is amphotericin B, if the size of the liposome is larger than desired, the liposome carrying the amphotericin B may be removed by the lungs or spleen as opposed to the desired site, namely, the liver.

One of the problems associated with the preparation of liposomes using the conventional "cast film" method is that usually a heterogeneous population of liposomes with respect to size is normally obtained. A more uniform size population can be obtained by use of ultrasonification of the liposomal material; however this generally results in the formation of liposomes of small size.

BRIEF DESCRIPITON OF THE INVENTION

In accordance with the present invention, a method is provided for preparing thin films of liposome components (also known as proliposomes), which are not subject to the physical stability problems set out above, and which may be employed to form liposome preparations immediately prior to administration.

In addition, the mean size of liposome preparations formed upon hydration of the proliposomes, produced by the method of the present invention will be more readily controlled than is possible by use of other techniques. Thus, it is possible in accordance with the method of the present invention to form the proliposomes in a manner such that the means size of the final hydrated liposome product can be controlled to suit the particular medicament to be carried by the liposome and the particular theraputic application and site.

The method of the present invention includes the steps of forming a solution in an organic solvent of at least one liposome-forming amphipathic lipid, optionally, at least one biologically active compound, and, optionally, at least one adjuvant, and employing the so-formed organic solution to coat a suitable water-soluble particulate carrier material (which carrier material is poorly soluble or insoluble in the organic solvent) to form a thin film of liposomal components (of controlled and desired thickness) on particles of the carrier material. The so-coated carrier material is also referred to as a proliposome.

In addition, in accordance with the present invention, a method is provided for forming a liposome preparation which method includes the step of exposing the water-soluble particulate material coated with the thin film of liposome components to water thereby causing the thin film of liposome components to hydrate and the carrier material to dissolve to give a liposome preparation, similar to that prepared by hydration of cast films with a solution of the carrier material, except that the so-formed liposome will have a desired size distribution.

Further, in accordance with the present invention, there is provided the intermediate formed above, that is the proliposome, which is comprised of the relatively stable particulate water-soluble carrier material coated with a thin film of liposome components (of controlled and desired thickness) and which is useful for forming the liposome preparation.

The problems associated with the physical stability of liposome dispersions on storage may be overcome by forming the aqueous dispersion of the coated powdered carrier material prior to administration. Additionally, the chemical integrity of the biologically active compounds and lipid components may be protected in the coated powdered preparations by the incorporation of antioxidants therein or packing the coated powdered material under inert atmospheres, for example. Moreover, the problems associated with size distribution of final hydrated liposome product as encountered in prior art liposomes formation are substantially eliminated by forming the proliposomes of the invention in a manner such that the film thickness, load or amount, for example, in $mg/m^2$ of lipid coated on the water-soluble particulate carrier material is controlled and in this way the final hydrated liposome product of desired mean size is attainable.

DETAILED DESCRIPITON OF THE INVENTION

In carrying out the method of the invention for preparing the particulate water-soluble carrier materials coated with a thin film or load of a predetermined amount of liposomal components, a predetermined amount of at least one liposome forming amphipathic lipid, optionally, at least one biologically active compound, and, optionally, at least one adjuvant are dissolved in an organic solvent and a predetermined amount of this organic solution is used to coat a suitable water-soluble carrier material which is poorly soluble or insoluble in the organic solvent. For low melting point liposome-forming amphipathic lipids (that is have a melting point below 50° C.), the optional biologically active compound and optional adjuvant may be directly dissolved in the lipid and this organic solution used to coat a suitable carrier material.

In general, in carrying out the method of the invention the liposomal components (that is the liposome-forming amphipathic lipid, optional biologically active compound and optional adjuvant) are dissolved in an organic solvent employing a weight ratio of liposomal components: organic solvent of within the range of from about 0.005:1 to about 0.5:1 and preferably from about 0.01:1 to about 0.25:1. Predetermined amounts of the organic solution is then used to coat particles of water-soluble carrier material to form a thin film or coating of such liposomal components on the particles of carrier material, which film will be equivalent to a loading on the particulate carrier of from about 0.5 $mg/m^2$ to about 100 $g/m^2$, and preferably from about 5 $mg/^2$ to about 50 $g/m^2$, depending upon the type of carrier material employed, (including its porosity and surface area) the type of lipid employed (including its content of neutral and/or negatively-charged phospholipid). It has been found that a predetermined degree of loading of the liposomal components on the carrier material, as outlined above, will facilitate ultimate formation of final liposome product of desired size, such as a mean diameter (or mass median volume-equivalent diameter) of within the range of from about 25 nm to about 12 um and preferably from about 100 nm to about 6 um.

It has also been found that the size of the final liposome product may be affected by the amount of neutral or negatively-charged phospholipid employed in forming the proliposomes. Thus, where neutral phospholipid such as egg lecithin and ergosterol are employed, it has been found that employing increasing amounts of such neutral phospholipids may cause increase in size in final liposome product, whereas where negatively-charged phospholipids such as, for example, dimyristoylphosphatidyl glycerol (sodium salt) is employed, it has been found that employing increasing amounts of such negatively-charged phospholipids may cause decrease in size in final liposome product.

In addition, it has been found that the pH of the hydration medium (over a range of 3 to 8), the ionic strength and the nature of the hydration medium (that is, the presence or absence of various salts for example, NaCl or RbCl) used in forming the final liposome product can have an effect on size of liposome product.

The lipid will be present in the organic solution (which may contain an additional organic solvent), to be used to coat the carrier material, in an amount of within the range of from about 1 to about 25% by weight, depending upon the solubility of the lipid in the solvent or solvent mixture used, and preferably from about 2.5 to about 12.5% by weight of such solution. The optional biologically active compound and optional adjuvant material will be present in the coating solution in varying amounts depending upon the nature of the particular compound and/or material employed.

The ratio of lipid to optional biologically active compound in the coating solution will depend upon the lipid solubility or binding of the biologically active compound used. Thus, the coating to be applied to the carrier material will normally contain a weight ratio of lipid:optional biologically active compound of within the range of from about 5:1 to about 1000:1 and preferably from about 10:1 to about 200:1 depending upon the particular biologically active compound to be employed. For example, where the biologically active compound is an anti-infective, such as an antibiotic or an anti-fungal agent, the lipid will be present in a weight ratio to the biologically active compound of within the range of from about 5:1 to about 1000:1 and preferably from about 10:1 to about 300:1. Where the biologically active compound is a contrast agent, the lipid will be present in a weight ratio to the contrast agent in an amount of within the range of from about 5:1 to about 1000:1 and preferably from about 10:1 to about 200:1.

The amounts of optional adjuvant material and biologically active material employed in the coating will comprise amounts conventionally employed in forming liposomes.

The amount of coating applied to the carrier material will depend upon physical characteristics of the carrier material such as surface area and isotonicity requirements, and the desired degree of loading or film thickness and ultimately the desired size of final liposome product. Thus, the coating will normally be present in a weight ratio to carrier material in an amount of within the range of from about 0.02:1 to about 6:1 and preferably from about 0.2:1 to about 5.5:1.

Any amphipathic lipid which is known to be suitable for preparing liposomes by known methods can be used in the method of this invention. Thus, a wide variety of lipids may be used but non-immunogenic and biodegradable neutral lipids would be preferred. Examples of suitable lipids are the neutral phospholipids, for example, natural lecithins, such as egg lecithin or soya bean lecithin, or synthetic lecithins such as saturated synthetic lecithins, for example, dimyristoylphosphatidyl choline, dimyristoylphophatidyl glycerol (e.g. Na salt), dipalmitoyl phosphatidyl choline or distearoyl phosphatidyl choline or unsaturated synthetic lecithins, such as dioleyl phosphatidyl choline or dilinoleyl phosphatidyl choline, with neutral egg lecithin and soya bean lecithin being preferred.

The biologically active compound employed in the present invention may be any compound of biological interest; for example, the compound may be a medicament, such as an anti-infective, for example, amphotericin B, ketoconazole, isoconazole, and benzyl penicillin, anti-tumor agents, such as 5-fluorouracil, methotrexate, actinomycin D, enzyme, hormone, contrast agent, or marker compound or NMR imaging agent, such as 4-succinyl-4-amino-2,2,6,6-tetramethylpiperidine-1-oxyl.

Examples of contrast agents suitable for use in the present invention include, but are not limited to the following: N,N'-bis[2-hydroxy-1-(hydroxymethyl)ethyl]-5-[(2-hydroxy-1-oxopropyl)-amino]-2,4,6-triiodo-1,3-benzenedicarboxamide (Bracco 15,000), metrizamide, diatrizoic acid, sodium diatrizoate, meglumine diatrizoate, acetrizoic acid and its soluble cationic salts, diprotrizoic acid and its soluble inorganic and organic cationic salts, iodamide, sodium iodipamide, meglumine iodipamide, iodohippuric acid and its soluble salts, iodomethamic acid and its soluble salts, iodopyracetiodo-2-pyridone-N-acetic acid and its soluble salts, 3,5-diiodo-4-pyridone-N-acetic acid (iodopyracet), 3,5-diiodo-4-pyridone-N-acetic acid diethanolamine salt, iodo-2-pyridone-N-acetic acid and its amine salt, iothalamic acid and its soluble salts, methanesulfonic acid, metrizoic acid and its soluble salts, sodium ipodate, ethiodized oil, iopanoic acid, iocetamic acid, tyropanoate sodium, iopydol, iophenoxic acid, iophendylate, and other chemically related iodinated contrast agents. Unless indicated otherwise, where applicable, the contrast agents which may be employed herein include inorganic, organic and cationic salts of the above contrast agent, such as the potassium salt, calcium salt, lithium salt, arginin salt, cystein salt, glycin salt, glycyl glycin salt, N-methyl glucosamine salt and other non-toxic aliphatic and alicyclic amines employed in preparing water soluble salts. Other X-ray contrast agents which may be employed herein are disclosed in German Offenlegungsschrift DT 2935-195.

The final liposome preparation containing a contrast agent prepared by the method of the invention may be employed as described in U.S. Pat. No. 4,192,859 which is incorporated herein by reference.

Other proteins and drugs available for use herein as optional biologically active compounds include steroids such as hydrocortisone, colchicine, insulin, cyclic AMP and α-thiodeoxyguanosine, chelating agents and cell modifying substances, such as antigens and interferon inducers.

The present invention is particularly useful in the case of lipid-soluble or lipid-bound biologically active compounds (which include some water-soluble compounds, such as proteins).

The method of this invention, like other methods of preparing liposomes, will result in partial incorporation of water-soluble biologically active compounds. Usually the formation of liposomes containing this type of compound is followed by removal of the unencapsulated material; however, in some instances coadministration of unencapsulated and liposomally entrapped biologically-active compounds may be advantageous.

The optional adjuvants suitable for use in the present invention may be:

(a) substances which are known to provide a negative charge on the liposomes, for example, egg phosphatidic acid or dicetyl phosphate;

(b) substances known to provide a positive charge, for example, stearyl amine, or stearyl amine acetate;

(c) substances shown to affect the physical properties of the liposomes in a more desirable way; for example, sterols such as cholesterol, ergosterol, phytosterol, sitosterol, sitosterol pyroglutamate, 7-dehydrocholesterol, lanosterol, or caprolactam, will affect membrane rigidity;

(d) substances known to have antioxidant properties to improve the chemical stability of the particulate carrier coated with liposome components, such as tocopherol, propyl gallate, ascorbyl palmitate, or butylated hydroxy toluene.

Suitable organic solvents for use in dissolving or aiding in dissolution of the above-mentioned mixture of lipid and optionally active compound and optional adjuvant ingredients include, but are not limited to, ethanol, methanol, chloroform, dichloromethane, diethyl ether, carbon tetrachloride, ethyl acetate, dioxane, cyclohexane and the like, with methanol, ethanol or chloroform being preferred.

The carrier material to be coated may be any water-soluble material which is suitable for oral or parenteral use, but is poorly soluble or insoluble in the organic solvent used for dissolving the mixture of lipid, optional active compound and optional adjuvant. Examples of such carrier materials include sodium chloride, lactose, dextrose, and sucrose, with sodium chloride being preferred.

Other examples of carrier material to be coated will include physiologically acceptable free-flowing powder which, even after processing, will remain substantially granular and free-flowing, will have a high water-solubility, for example, in excess of about 10% by weight in water and a rapid dissolution rate in water, for example, complete solution in 3 to 4 minutes at 40° C., is suitable for oral or parenteral use, is poorly soluble or insoluble in the organic solvent, and will preferably form an isotonic solution in water in a concentration range of from about 1 to about 10% w/v, and preferably from about 3 to about 7% w/v; examples of such additional carrier materials include sorbitol, mannitol, xylitol, or naturally occurring amino acids such as arginine or glycine, with sorbitol being preferred.

It may be advantageous to use micronized forms of the carrier materials (that is, having an average particle size of less than about 10 microns) as the high surface area would facilitate the hydration and dissolution of the liposomal components. However, the carrier materials may have an average particle size of up to and in excess of 500 microns and still be useful. The amount of carrier material used may be adjusted so that the final reconstituted suspension is iso-osmotic with the blood, although for small volume injections this may not be necessary. As a suitable aqueous medium for dispersion distilled water, isotonic saline or buffer solution may be used, the temperature of which may be modified to exceed the phase transition temperature of the lipid components used in formulation.

The liposomal components (excluding the biologically active compound) preferably are binary mixtures of lipid such as egg lecithin and a sterol selected from the group listed hereinabove (e.g., ergosterol or cholesterol), or ternary mixtures of such lipid, dicetyl phosphate, or other negatively-charged phospholipid such as dimyritoylphosphatidyl glycerol, and a sterol selected from the group listed hereinabove, in the preferred molar ratios of 7:2:1, respectively. The molar percentage of lipid may range from about 55 to about 95% and the sterol from about 5 to about 35% based on a binary mixture. The molar percentage of lipid may range from about 50% to about 80%, the dicetyl phosphate from 0 to about 30%, and the sterol from about 5 to about 30%, based on a ternary lipid mixture. The lipid is employed to take advantage of its property of swelling in salt solutions. Dicetyl phosphate or dimyristoylphosphatidyl glycerol has the property of imparting a negative charge to the lipid membranes so that the mutual repulsive action of opposing channel surfaces widens the channels.

The components which constitute the liposomal mixture are commercially available or may readily be prepared.

Coating of the carrier material may be achieved by applying organic solutions of liposomal components dissolved either in the lipid phase or in a suitable organic solvent followed by solvent removal. Alternatively, a solution of liposomal components may be spray dried on the carrier material. By suitable containment and sterilization of component materials, sterile carrier material coated with the liposomal components (a proliposome) is produced. The coated carrier material of the invention may be packed in sterile unit dose vials under aseptic conditions and reconstituted immediately prior to use by the physician by hydration of the lipid film (above the phase transition temperature of the lipids) together with dissolution of the particulate carrier material to form a isotonic liposomal suspension.

The final liposome formulations prepared as described above may be administered parenterally, for example, intravenously, as well as orally and topically.

The following Examples represent preferred embodiments of the present invention.

EXAMPLE 1

Five hundred and ten milligrams (510 mg) of dextrose (anhydrous) were placed in a 100 ml round bottom flask and 40 mg of egg lecithin dissolved in 3 ml of chloroform added in 3×1 ml portions. After each portion addition, the solvent was removed under vacuum from the rotating flask. Microscopic examination of the powder showed that the dextrose particles were coated with lipid material.

The so-formed coated carrier may be packaged and stored in sterile unit dose vials under aseptic conditions and reconstituted immediately prior to use.

Distilled water (5 ml) was added to a portion of the above dextrose preparation coated with phospholipid (225 mg) in a vial and the mixture heated to 60°0 C., for one minute, then agitated by hand to achieve the final dispersion. The size distribution of the liposome preparation was log-normal as determined using a Coulter Counter with a mass median volume equivalent diameter of 5.3 $\mu$m and a geometric standard deviation of 1.58.

The above liposome preparation is similar to those prepared by hydration of cast films with a solution of the carrier material.

EXAMPLE 2

Egg lecithin (2.0 g), ergosterol (0.5 g) and amphotericin B (50.0 mg) were dissolved in methanol (10 ml). Lactose (13.0 g) was placed in a 250 ml round bottom flask and the above solution added in 2 ml portions. After each portion addition, the solvent was removed under vacuum from the rotating flask. Microscopic examination of the powder showed that the lactose particles were coated with lipid material.

The so-formed coated carrier may be packaged and stored in sterile unit dose vials under aseptic conditions and reconstituted immediately prior to use by the physician as follows.

Water for injection (10 ml) was added to a portion of the above lactose preparation coated with liposomal components (0.775 g) in a vial and the mixture heated to about 70° C. in a water bath to aid dissolution of the carrier material. Shaking of the vial caused the preparation to disperse resulting in a milky dispersion. The size distribution of the liposomes formed was log-normal as determined using a Coulter counter with a mass median volume equivalent diameter of 2.5 $\mu$m and a geometric standard deviation of 1.56.

The liposome preparation containing the amphotericin B is similar to those prepared by hydration of cast films with a solution of the carrier material.

EXAMPLE 3

Five hundred and ten milligrams (510 mg) of dextrose (anhydrous) were placed in a 100 ml round bottom flask and 40 mg of egg lecithin dissolved in 3 ml of chloroform added in 3×1 ml portions. After each portion addition, the solvent was removed under vacuum from the rotating flask. Microscopic examination of the powder showed that the dextrose particles were coated with lipid material.

The so-formed coated carrier may be packaged and stored in sterile unit dose vials under aseptic conditions and reconstituted immediately prior to use.

Distilled water (5 ml) was added to a portion of the above dextrose preparation coated with phospholipid (225 mg) in a vial and the mixture heated to 60° C. for one minute, then agitated by hand to achieve the final dispersion. The size distribution of the liposome preparation was log-normal as determined using a Coulter Counter with a mass median volume equivalent diameter of 5.3 $\mu$m and a geometric standard deviation of 1.58.

The above liposome preparation is similar to those prepared by hydration of cast films with a solution of the carrier material.

EXAMPLE 4

Egg lecithin (2.0 g), ergosterol (0.5 g) and amphotericin B (50.0 mg) were dissolved in methanol (10 ml). Lactose (13.0 g) was placed in a 250 ml round bottom flask and the above solution added in 2 ml portions. After each portion addition, the solvent was removed under vacuum from the rotating flask. Microscopic examination of the powder showed that the lactose particles were coated with lipid material.

The so-formed coated carrier may be packaged and stored in sterile unit dose vials under aseptic conditions and reconstituted immediately prior to use by the physician as follows.

Water for injection (10 ml) was added to a portion of the above lactose preparation coated with liposomal components (0.775 g) in a vial and the mixture heated to about 60°–70° C. in a water bath to aid dissolution of the carrier material. Shaking of the vial caused the preparation to disperse resulting in a milky dispersion. The size distribution of the liposomes formed was log-normal as determined using a Coulter Counter with a mass median volume equivalent diameter of 2.5 $\mu$m and a geometric standard deviation of 1.56.

The liposome preparation containing the amphotericin B is similar to those prepared by hydration of cast films with a solution of the carrier material.

EXAMPLE 5

Egg lecithin (89 mg), cholesterol (24 mg), dicetyl phosphate (12.4 mg) and amphotericin B (2.6 mg) were dissolved in methanol (10 ml). Sorbitol (500 mg) was placed in a 250 ml round bottom flask and the above solution added in 2 ml portions. After each portion addition, the solvent was removed under vacuum from the rotating flask. Microscopic examination of the powder showed that the sorbitol particles were coated with lipid material.

The so-formed coated carrier may be packaged and stored in sterile unit dose vials under aseptic conditions and reconstituted immediately prior to use by the physician as follows.

Water for injection (10 ml) was added to a portion of the above sorbitol preparation coated with liposomal components (0.628 g) in a vial and the mixture heated at 60°–70° C. to dissolve the carrier material and form a liposome preparation.

The liposome preparation containing the amphotericin B is similar to those prepared by hydration of cast films with a solution of the carrier material.

EXAMPLE 6

Egg lecithin (121 mg), ergosterol (5 mg) and amphotericin B (5 mg) were dissolved in methanol (10 ml). Sorbitol (500 mg) was placed in a 250 ml round bottom flask and the above solution added in 2 ml portions. After each portion addition, the solvent was removed under vacuum from the rotating flask. Microscopic examination of the powder showed that the sorbitol particles were coated with lipid material.

The so-formed coated carrier may be packaged and stored in sterile unit dose vials under aseptic conditions and reconstituted immediately prior to use by the physician as follows.

Water for injection (10 ml) was added to a portion of the above sorbitol preparation coated with liposomal components (0.631 g) in a vial and the mixture heated at 60°–70° C. to dissolve the carrier material and form a liposome preparation.

The liposome preparation containing the amphotericin B is similar to those prepared by hydration of cast films with a solution of the carrier material.

EXAMPLE 7

Determination of Effect of Negatively-charged Phospholipids on Size of Liposomes Derived from Proliposomes A. Preparation of amphotericin B (AmB)/lipid/sterol) in organic solutions A solution/suspension of amphotericin B in methanol was prepared at 1 mg/ml; extended shaking/sonication was required to achieve adequate levels of drug in solution. Undissolved material was removed by passing the suspension through a 0.2 $\mu$m filter (Millipore GVWP). Amphotericin B concentration of the filtrate was determined spectrophotometrically. In general, a final concentration of about 0.8 mg/ml was obtained. Dimyristoylphosphatidyl chlorine (DMPC) and dimyristoylphosphatidyl glycerol (Na salt) (DMPG) (molar ratio=7:3) were dissolved in chloroform such that the total weight of lipid was 16-fold greater than the total weight of amphotericin B in solution. This phospholipid:drug ratio was chosen to avoid saturation of the lipid bilayers with amphotericin B. Saturation of the bilayers with a water-insoluble drug may be manifested by the presence of extra-liposomal crystalline material, often observable by light microscopy. Thus, for this formulation, an encapsulation efficiency approaching 100% was obtained. The volume of chloroform utilized was adjusted so that the final volume ratio of methanol to chloroform was 2:1.

B. Egg lecithin/ergosterol/amphotericin B organic solution

In general, a similar procedure to the one outlined above was utilized except ergosterol and egg lecithin were dissolved in the methanolic solution of amphotericin B (chloroform was omitted). A molar ratio of 28:2.3:1 (egg lecithin:ergosterol:amphotericin B) was utilized throughout.

C. Preparation of Proliposomes

(1) Sorbitol-based proliposome

In a typical batch, 10 g sorbitol (total pore area of 125–500 μm cut was 33.1 m$^2$/g) was placed in a 100 ml round-bottomed flask. A modified rotary evaporator (Büchi Rotavapor-R) was evacuated (93–101 kPa) and the rotating flask lowered into a water bath at 35°–45° C. (dependent upon the nature of the lipid and carrier). A weight of the lipid/amphotericin B/(sterol) solution equivalent to half the weight of sorbitol in the flask was introduced into the tumbling powder bed via the feed line running through the condenser unit. Evaporation was allowed to proceed until the powder bed temperature reached about 15° C. and began to rise at which point a second aliquot of solution was introduced. This process was repeated until all the solution had been deposited onto the sorbitol. At no time was the powder bed allowed to become over-wet (such that a slurry was formed), nor was the unit operated in the absence of a vacuum; failure to observe these precautions resulted in complete dissolution of the sorbitol. After addition of the final aliquot, evaporation was continued until the powder bed temperature began to rise substantially (to about 30° C.). At this point, the material was removed from the flask and passed through a 950 μm aperature stainless steel sieve. The material was then dried overnight in a desiccator in vacuo at room temperature. After drying, material <75 μm and >600 μm was removed by sieving and was discarded; the remaining material was packaged under nitrogen in unit dose vials such that upon hydration with water an isotonic solution would be formed (i.e., equivalent to 5% w/v sorbitol).

The loading of liposomal components onto sorbitol was approximately 7.9 mg/m$^2$.

Differential scanning calorimetry (employing Dupont Instruments Model 910 in conjunction with a Dupont 990 Computer/Thermal Analyzer) of egg lecithin/ergosterol/AmB proliposomes revealed the phospholipid endotherm to give an extrapolated onset temperature of −14.1° C. with a phase transition temperature (Tm) of −6.8° C. Thus, proliposomes of this formulation were hydrated at room temperature (20° C.), substantially above the Tm of the phospholipid. In contrast, proliposomes composed of DMPC and DMPG (Tm=23° C.) required hydration above 30° C. (preferably 37° C.). Differential scanning calorimetry of this formulation revealed a broadening of the phospholipid endotherm (by comparison with pure phospholipids) resulting in an extrapolated onset temperature of 20.6° C.

(2) Sodium chloride-based proliposomes

The procedure adopted was essentially the same as for sorbitol-based proliposomes, with the following exceptions: first, in a typical batch, 1.8 g sodium chloride was used (rather than 10 g sorbitol) so that after addition of the appropriate amount of water, the resulting liposome suspension would be iso-tonic. Second, the reduction in carrier weight necessitated a reduction in the volume of lipid/AmB solution added during manufacture. Third, a weight ratio of sodium chloride to total lipid of 1:5.4 was found optimal.

D. Results

(1) Sorbitol-based Proliposomes Composed of Lipid/sterol/AmB

Scanning electron micrographs of both uncoated sorbitol and sorbitol coated with egg lecithin/ergosterol/AmB show that the porous structure of the sorbitol appeared to be maintained after proliposome manufacture, thus suggesting that the majority of the lipid/ergosterol/AmB was within the matrix of the granules.

Upon hydration at room temperature, sorbitol-based proliposomes composed of egg lecithin/ergosterol/AmB formed multilamellar liposomes with a mass median volume equivalent diameter of approximately 1.8 μm as determined by Coulter Counter; this size was a consistent feature of the formulation (when manufactured under defined conditions).

(2) Sorbitol-based Proliposomes Composed of DMPC/DMPG/AmB (molar ratio=7:3:0.52) hydrated (at 37° C.) to form liposomes with a mean diameter of 120 nm (polydispersity=0.31) (analysis by photon correlation spectroscopy (PCS), employing a Malvern 4600M with a 35 mW helium-neon laser (Spectra Physics Model 124B)) substantially smaller than those composed of egg lecithin. Since the extent of loading onto carrier was the same for both formulation, one reason for the difference in particle size was thought to be due to the presence of charged phospholipid (DMPG) in the DMPC/DMPG/AmB formulation. To test this hypothesis, a variety of proliposomal formulations were prepared consisting of various DMPC:DMPG ratios (at a constant lipid to sorbitol ratio). Upon hydration at 37° C., liposome particle size was measured by Coulter Counter. Results are presented in Table I set out below and indicate that as the level of the negatively charged lipid increases, so mean liposome size decreases. Thus, at a constant lipid to sorbitol loading, the size of liposomes derived from proliposomes may be modified by the content of negatively-charged phospholipid.

TABLE I

| EFFECT OF DMPC:DMPG RATIO ON THE SIZE OF LIPOSOMES DERIVED FROM PROLIPOSOMES (AS DETERMINED BY COULTER COUNTER ANALYSIS) | |
|---|---|
| Molar Ratio DMPC:DMPG | Mass Median Volume Equivalent Diameter (μm ± SD) |
| 25:1 | 1.5 ± 1.4 |
| 50:1 | 3.0 ± 2.8 |
| 100:1 | 3.5 ± 2.4 |

TABLE I-continued

EFFECT OF DMPC:DMPG RATIO ON THE SIZE OF LIPOSOMES DERIVED FROM PROLIPOSOMES (AS DETERMINED BY COULTER COUNTER ANALYSIS)

| Molar Ratio DMPC:DMPG | Mass Median Volume Equivalent Diameter ($\mu m \pm$ SD) |
|---|---|
| 250:1 | 4.9 ± 4.1 |

One of the simplest and most convenient procedures for preparing liposomes is that of casting a dry lipid film on the inside of a round-bottomed flask, by evaporation from organic solvent. Subsequent hydration of dry lipid by aqueous phase (above the phase transition temperature of the lipid) results in the formation of liposomes. Early experiments had indicated that the size of liposomes derived from DMPC/DMPG/AmB (7:3:0.52) cast films deposited on the inside wall of a round-bottomed flask (at a loading of about 30 g/m$^2$) had typical mass median volume equivalent diameters of approximately 2.0 $\mu$m. In contrast, liposomes derived from sorbitol-based proliposomes of similar formulation (at a loading of 7.9 mg/m$^2$) had mean sizes of 100-150 nm.

The approach taken therefore, was to determine whether an increase in lipid film thickness on a proliposome carrier results in an increase in mean liposome size. To achieve this aim, a relatively non-porous carrier, namely, sodium chloride, was utilized. The surface area of sodium chloride 315-600 $\mu$m size cut was determined to be 0.12 m$^2$/g. DMPC/DMPG/AmB were coated onto the carrier to a loading of about 47 g/m$^2$ (comparable to that of the conventional cast film procedure). Hydration of the sodium chloride-based proliposomes with water at 37° C. resulted in the formation of liposomes of similar mass median volume equivalent diameter to those produced by the conventional cast film method (i.e., approximately 1.8 $\mu$m).

To eliminate the possibility that sodium chloride per se was responsible for the substantial increase in liposome size, sorbitol based proliposomes were hydrated in normal saline while cast lipid films were hydrated in 5% w/v sorbitol. While minor changes in particle size were seen, nothing as substantial as that displayed by altering lipid film thickness was observed. Thus, a degree of control over liposome size could be obtained by considering the nature of the carrier, the type of lipid and its final degree of loading.

Further, marked differences in liposome size could be achieved with the same liposome formulation but with differences in lipid loading (the nature of the different carrier materials had only a small effect on liposome size in this study).

With the egg lecithin/ergosterol/amphotericin B formulation, further evidence of the importance of lipid film thickness was obtained by sampling the proliposome batch at various points in the process. Thus, a mass median volume equivalent diameter of 3.1 $\mu$m was attained at 75% of the optimal loading, whereas a mean size of 4.25 $\mu$m was achieved at 100% loading.

EXAMPLE 8

Proliposomes were prepared as described in Example 7 on particulate sorbitol sieved to obtain a 125-500 $\mu$m size cut. The sorbitol was coated with phospholipids/sterol/drug, that is, DMPC:DMPG:Erg:AmB.

(1) Determination of Effect of pH of Hydration Liquid on Liposome Size

The effect of pH on the hydrated liposome product may have an effect on liposome size with subsequent effects on tissue distribution and efficacy. As amphotericin proliposomes contain no buffer or other pH controlling material and are hydrated with water for injection (with pH limits of 5.0-7.0 in USP XXI), size variation of the resultant liposomes could be produced if pH has an effect. Proliposomes were hydrated in constant ionic strength buffers over the range pH 3-8 for evaluation of pH of the hydration medium on the size of liposomes produced (Table II).

TABLE I

EFFECT OF HYDRATION MEDIUM pH ON THE SIZE OF LIPOSOMES DERIVED FROM DMPC/DMPG/ERG/AmB PROLIPOSOMES

| pH | Mean Liposome Size ($\mu$m) |
|---|---|
| 3 | 1.2 |
| 4 | 0.2 |
| 5 | ~0.25 |

At pH 3.0 very large liposomes appeared to form but much smaller liposomes occurred at pH 4.0 and above, with some slight changes over the range pH 4.0-8.0. The effect at pH 3.0 may have been due to protonation of the acidic function of DMPG, resulting in destabilisation of the liposome structure. An effect of charge may have been involved. The effect of protonation of DMPG is to reduce the charge on the liposomes and this may be responsible for the increase in liposome size at low pH values.

The increase in size was noted over the range pH 4.0-6.0. This may have been due to increase in amounts of available sodium counter ion from the buffer, as its sodium content increases with increasing pH. The effect is explained in detail below when considering ionic strength. An increase in size between pH 6.0 and pH 8.0 possibly relates to charge changes on the liposomes resulting from deprotonation of other species.

(2) Determination of Ionic Strength on Liposome Size

Further to the pH studies the effect of increasing the ionic strength by addition of salts to a constant pH system was evaluated. This would be important if hydration with media other than water for injection was employed and varied volumes of hydration media were used. As can be seen from the sodium chloride data (Table III), there is an increase in liposome size as the amount of sodium chloride in the hydration medium increases. This can be explained in terms of the sodium ions acting as counter ions to the negatively charged phosphatidylglycerol in the liposomes resulting in a reduction of the net charge on the liposomes.

TABLE III

EFFECT OF HYDRATION MEDIUM COMPOSITION/IONIC STRENGTH ON THE SIZE OF LIPOSOMES DERIVED FROM DMPC/DMPG/Erg/AmB PROLIPOSOMES

| | NaCl | |
|---|---|---|
| Ionic Strength (M) | | Mean Liposome Size |
| ~0.04 | | 0.3 |
| ~0.08 | | 0.34 |
| 0.15 | | 0.32 |
| 0.3 | | 0.43 |
| | RbCl | |

TABLE III-continued

EFFECT OF HYDRATION MEDIUM COMPOSITION/IONIC STRENGTH ON THE SIZE OF LIPOSOMES DERIVED FROM DMPC/DMPG/Erg/AmB PROLIPOSOMES

| Ionic Strength | Mean Liposome Size |
| --- | --- |
| ~0.04 | 0.16 |
| ~0.08 | 0.21 |
| 0.15 | 0.2 |
| 0.3 | 0.25 |

As seen in Table III, regarding rubidium chloride, the liposome size effect for a given amount of salt is lower than for sodium chloride suggesting that a higher net charge remains on the liposomes. As the hydrated rubidium ion is very much larger than the sodium ion there may be steric effects preventing it accessing as many potential binding sites within the bilayers of the liposomes. This would result in a higher net charge on the liposome than in the sodium chloride case and thus give rise to smaller liposomes.

As seen from the above results, marked changes in liposome size can be induced by changes in the pH of the hydration medium (over the pH range 3–8). However, with the pH limits set for water for injection (pH 5.0–7.0) little effect of pH on liposome size was noted. Ionic strength and nature of the hydration medium can have a marked effect on liposome size.

EXAMPLE 9

The following was carried out to illustrate the effect that the amount of loading or film thickness of lipid, adjuvant and medicament deposited on a particulate carrier (proliposomes) has on the size of liposomes derived from such proliposomes.

Proliposomes were prepared in a manner similar to that described in Example 7 Parts B and C(1). A methanol solution (400 ml) containing egg lecithin (4.84 g), ergosterol (0.2 g) and amphotericin B (0.2 g) was prepared.

Sorbitol (20 g, 125–500 μm size cut) was placed in a round-bottom flask. A modified rotary evaporator was evacuated and the rotating flask lowered into a water bath at ~40° C. A portion of the above organic solution (10%, that is, 40 ml) was sprayed onto the heated tumbling powder bed in vacuo. After drying, a portion of the proliposomal material was removed for particle size analysis of resultant liposomes.

Further aliquots of methanolic solution were then sprayed onto the remaining powder bed so that loadings of 25, 50, 75 and 100% were achieved; samples of proliposomal material were removed at each stage for size analysis.

Due account was taken for the material removed at each stage by reducing the amount of added methanolic solution accordingly.

Each of the proliposomal materials (10, 25, 50, 75 and 100% loading) was then hydrated by mixing with distilled water at 20°–25° C. in a manner similar to that described in Example 1. The mass median volume-equivalent diameters (microns) of the liposomes so produced were then determined. The % loading or relative film thickness (for each proliposome material) and the size of the liposomes derived from each of such proliposome materials is set out in Table IV.

TABLE IV

| % Loading | Mass medium volume Equivalent diameter (microns) |
| --- | --- |
| 10 | 1.6 ± 1 |
| 25 | 2.0 ± 1.2 |
| 50 | 2.5 ± 1.4 |
| 75 | 3.2 ± 1.5 |
| 100 | 5.3 ± 2 |

As can be seen from the results set out in Table IV, where neutral lipids such as egg lecithin (and presumably other neutral lipid formulation, such as egg lecithin and cholesterol are employed), the mean liposome size increases with increase in lipid loading.

From the above results, it is clear that size of the final liposome preparation is dependent upon the loading or relative film thickness of the proliposome. Thus, size of the final liposome may be controlled by controlling the loading or relative film thickness of the proliposome. However, as seen in Example 7, as the level of negatively-charged phospholipids increases, the size of liposomes derived therefrom decreases.

What is claimed is:

1. A method for preparing a stable liposome precursor in the form of a thin film of liposomal components of predetermined amount coated on a water-soluble particulate carrier material which is suitable for intravenous use, which liposome precursor may be hydrated to form a liposome product of controlled and acceptable mean size, which comprises forming a solution, in an organic solvent, of at least one liposome-forming lipid selected from the group consisting of a phospholipid, a natural lecithin and a synthetic lecithin in an amount of from about 1 to about 25% by weight of the organic solution, optionally, at least one biologically active compound which is medicament, protein, enzyme, hormone or diagnostic agent, and, optionally, at least one adjuvant which imparts advantageous properties to the final liposome preparation, and coating a particulate water-soluble carrier material which is suitable for intravenous use and is substantially insoluble in said organic solvent, with the so-formed organic solution to form a thin film of liposomal components of predetermined desired amount on said carrier material which thin film contains a ratio of lipid:optional biologically active compound (where present) of within the range of from about 0.5:1 to about 1000:1, which so-coated particulate water-soluble carrier material may be exposed to a hydration medium to form a final hydrated liposome product of controlled and desired mean size.

2. The method as defined in claim 1 wherein the thin film of liposomal components, coated on the particulate carrier is present in an amount within the range of from about 0.5 mg/m$^2$ to about 100 g/m$^2$ of carrier material so that the final hydrated liposome product will have a desired mean size distribution of within the range of from about 25 nm to about 12 μm.

3. The method as defined in claim 1 wherein the organic solution is formed by dissolving said lipid, optionally, said biologically active compound and, optionally, said adjuvant in one or more organic solvents.

4. The method as defined in claim 1 wherein the organic solution is formed by dissolving the optional biologically active compound and optional adjuvant in said lipid, said lipid being of the low melting point liposome-forming type.

5. The method as defined in claim 1 wherein the particulate carrier material is coated with said solution by suspending the carrier material in the solution of liposomal components and spray drying the coated carrier material.

6. The method as defined in claim 1 wherein the lipid is a phospholipid.

7. The method as defined in claim 5 wherein the phospholipid is a natural or synthetic lecithin.

8. The method as defined in claim 1 wherein the lipid is dimyristoylphosphatidyl choline, alone or in combination with dimyristoylphosphatidyl glycerol.

9. The method as defined in claim 1 wherein said solution includes a biologically active compound which is a medicament, contrast agent, enzyme, hormone, or marker compound.

10. The method as defined in claim 1 wherein the adjuvant is egg phosphatidic acid, dicetyl phosphate, or stearyl amine.

11. The method as defined in claim 1 wherein the adjuvant is a sterol.

12. The method as defined in claim 8 wherein the adjuvant also includes a sterol selected from the group consisting of cholesterol, phytosterol, ergosterol, sitosterol, sitosterol, 7-dehydrocholesterol or lanosterol.

13. The method as defined in claim 1 wherein said carrier is sodium chloride, lactose, dextrose, or sucrose.

14. The method as defined in claim 1 wherein said carrier material has a watersolubility in excess of 10% by weight, a rapid dissolution rate in water, and will form an isotonic solution in water in a concentration of from about 1 to about 10% w/v.

15. The method as defined in claim 3 wherein said carrier material is sorbitol, mannitol, or xylitol or a naturally occurring amino acid.

16. The method as defined in claim 1 wherein the carrier material is sorbitol or sodium chloride.

17. The method as defined in claim 1 wherein the organic solvent is ethanol, methanol, chloroform, dichloromethane, diethyl ether, carbon tetrachloride, ethyl acetate, dioxane or cyclohexane.

18. The method as defined in claim 14 wherein the solvent is methanol, ethanol or chloroform.

19. The method as defined in claim 1 wherein the biologically active compound is amphotericin B.

20. The method as defined in claim 1 wherein the lipid is egg lecithin, dimyristoylphosphatidyl choline alone or in admixture with dimyristoylphosphatidyl glycerol, the optional adjuvant is ergosterol, cholesterol or dicetyl phosphate, and the carrier material is sorbitol or sodium chloride.

21. The method as defined in claim 20 wherein the lipid is egg lecithin, and the adjuvant is ergosterol.

22. A stable liposome precursor which when mixed with water forms a liposome preparation of controlled and acceptable mean size distribution, comprising a water-soluble particulate carrier material suitable for intravenous use coated with a predetermined amount of a thin film of liposomal components comprised of at least one liposome-forming lipid selected from the group consisting of a phospholipid, a natural lecithin and a synthetic lecithin, optionally, at least one biologically active compound which is a medicament, protein, enzyme, hormone or diagnostic agent, and, optionally, at least one adjuvant which imparts advantageous properties to the final liposome preparation and which thin film contains a ratio of lipid:optional biologically active compound (where present) of within the range of from about 0 5:1 to about 1000:1.

23. The stable liposome precursor as defined in claim 21 wherein the thin film of liposomal components is present in an amount within the range of from about 0.5 mg/m$^2$ to about 100 g/m$^2$ of carrier material so that the final hydrated liposome product will have a desired mean size distribution of within the range of from about 25 nm to about 12 μm.

24. A stable liposome precursor which when mixed with water forms a liposome preparation of controlled and acceptable mean size, comprising a water-soluble particulate carrier material suitable for intravenous coated with a predetermined amount of a thin film comprised of at least one liposome-forming lipid selected from the group consisting of a phospholipid, a natural lecithin and a synthetic lecithin, optionally, at least one biologically active compound which is a medicament, protein, enzyme, hormone or diagnostic agent, and, optionally, at least one adjuvant which imparts advantageous properties to the final liposome preparation, prepared by the method as defined in claim 1.

25. The method as defined in claim 21 including a biologically active compound which is amphotericin B.

26. The stable liposome precursor as defined in claim 22 including a biologically active compound.

27. The stable liposome precursor as defined in claim 26 wherein the biologically active compound is amphotericin B.

28. The stable liposome precursor as defined in claim 22 wherein the lipid is egg lecithin, the adjuvant is ergosterol and the biologically active compound is amphotericin B.

* * * * *